(12) United States Patent
Smith

(10) Patent No.: US 8,567,081 B2
(45) Date of Patent: Oct. 29, 2013

(54) APPARATUS AND METHOD FOR IMAGING FEET

(75) Inventor: Christopher E. Smith, Custer, WA (US)

(73) Assignee: Northwest Podiatric Laboratory, Inc., Blaine, WA (US)

( * ) Notice: Subject to any disclaimer, the term of this patent is extended or adjusted under 35 U.S.C. 154(b) by 594 days.

(21) Appl. No.: 12/924,669

(22) Filed: Sep. 30, 2010

(65) Prior Publication Data

US 2012/0053490 A1 Mar. 1, 2012

Related U.S. Application Data

(60) Provisional application No. 61/402,601, filed on Aug. 31, 2010.

(51) Int. Cl.
*A61B 5/107* (2006.01)

(52) U.S. Cl.
USPC ................................. 33/515; 33/3 A

(58) Field of Classification Search
CPC ............................. A61B 5/1077; A61B 5/0555
USPC ....... 33/515, 227–228, 3 A; 36/112; 382/307, 382/317, 203, 190, 195, 199; 600/415, 592; 378/208–209; 348/135
See application file for complete search history.

(56) References Cited

U.S. PATENT DOCUMENTS

| | | | | |
|---|---|---|---|---|
| 2,082,912 A | * | 6/1937 | Russell | 33/3 A |
| 2,657,463 A | * | 11/1953 | Spencer Burdell D | 33/3 A |
| 2,795,953 A | * | 6/1957 | Gabriel Makowsky | 73/172 |
| 3,192,627 A | * | 7/1965 | Levitt Milton R et al. | 33/3 C |
| 3,766,384 A | * | 10/1973 | Anderson | 378/209 |
| 4,267,728 A | * | 5/1981 | Manley et al. | 73/172 |
| 4,604,807 A | * | 8/1986 | Bock et al. | 33/3 C |
| 4,662,079 A | | 5/1987 | Graf et al. | |
| 4,745,290 A | * | 5/1988 | Frankel et al. | 250/559.17 |
| 5,025,476 A | * | 6/1991 | Gould et al. | 382/115 |
| 5,164,793 A | * | 11/1992 | Wolfersberger et al. | 356/607 |
| 5,541,515 A | * | 7/1996 | Tsujita | 324/318 |
| 5,640,779 A | | 6/1997 | Rolloff | |
| 5,671,055 A | * | 9/1997 | Whittlesey et al. | 356/602 |
| 5,689,446 A | * | 11/1997 | Sundman et al. | 702/167 |
| 5,753,931 A | * | 5/1998 | Borchers et al. | 250/559.22 |
| 5,804,830 A | * | 9/1998 | Shafir | 250/559.22 |
| 6,006,412 A | * | 12/1999 | Bergmann et al. | 29/407.04 |
| 6,160,264 A | * | 12/2000 | Rebiere | 250/559.22 |
| 6,163,971 A | * | 12/2000 | Humphries, Jr. et al. | 33/515 |
| 6,205,230 B1 | | 3/2001 | Sundman et al. | |
| 6,430,831 B1 | * | 8/2002 | Sundman | 33/515 |

(Continued)

*Primary Examiner* — Peter Macchiarolo
*Assistant Examiner* — Tania Courson
(74) *Attorney, Agent, or Firm* — Todd N. Hathaway

(57) ABSTRACT

An apparatus and method for determining contours of a patient's foot. The apparatus includes an alignment section that orientates the foot relative to an optical imaging section. The alignment section includes at least one support member located proximate a focal length of the imaging section, that engages the plantar surface substantially only in the immediate area of the fifth metatarsal head of the foot. The support generates a dorsally-directed load that locks the midtarsal joint. The alignment section further includes a heel stirrup and a laser beam or other reference line for aligning the second metatarsal head with the distal one-third of the lower leg, to place the subtalar joint in a neutral condition. The foot is thus suspended in space such that the imaging section is able to obtain an accurate measurement of the plantar surface without distortion of the soft tissues or bone structure of the foot.

25 Claims, 13 Drawing Sheets

(56) References Cited

U.S. PATENT DOCUMENTS

| | | | |
|---|---|---|---|
| 6,546,356 B1 * | 4/2003 | Genest | 702/153 |
| 6,550,149 B2 | 4/2003 | Dowdell | |
| 6,661,240 B1 * | 12/2003 | Johnson et al. | 324/662 |
| 6,829,377 B2 * | 12/2004 | Milioto | 382/128 |
| 6,909,513 B1 * | 6/2005 | Fujita et al. | 356/601 |
| 6,969,193 B1 * | 11/2005 | Pigg | 378/180 |
| 7,051,452 B2 | 5/2006 | Brooks | |
| 7,926,363 B2 * | 4/2011 | Miller et al. | 73/862.041 |
| 7,952,727 B2 * | 5/2011 | Sundman et al. | 356/601 |
| 2002/0138923 A1 | 10/2002 | Shaffeeullah | |
| 2002/0157266 A1 | 10/2002 | Dowdell | |
| 2005/0061332 A1 | 3/2005 | Greenawalt et al. | |
| 2005/0261869 A1 | 11/2005 | Leyerer et al. | |
| 2006/0076700 A1 | 4/2006 | Phillips | |
| 2006/0283243 A1 | 12/2006 | Peterson | |

* cited by examiner

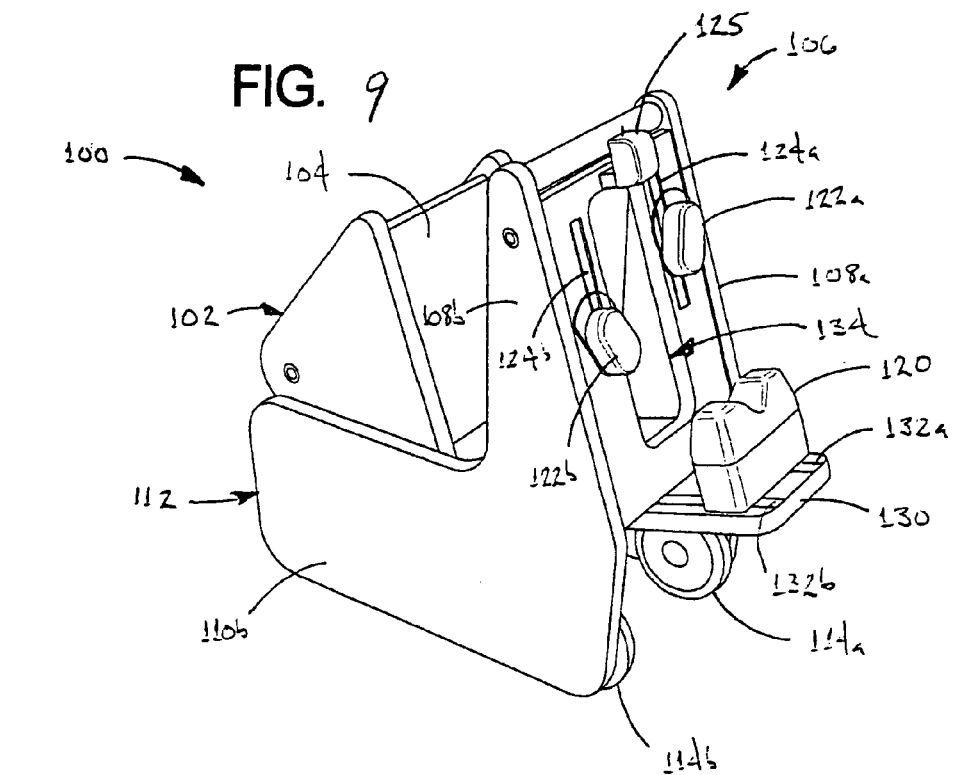
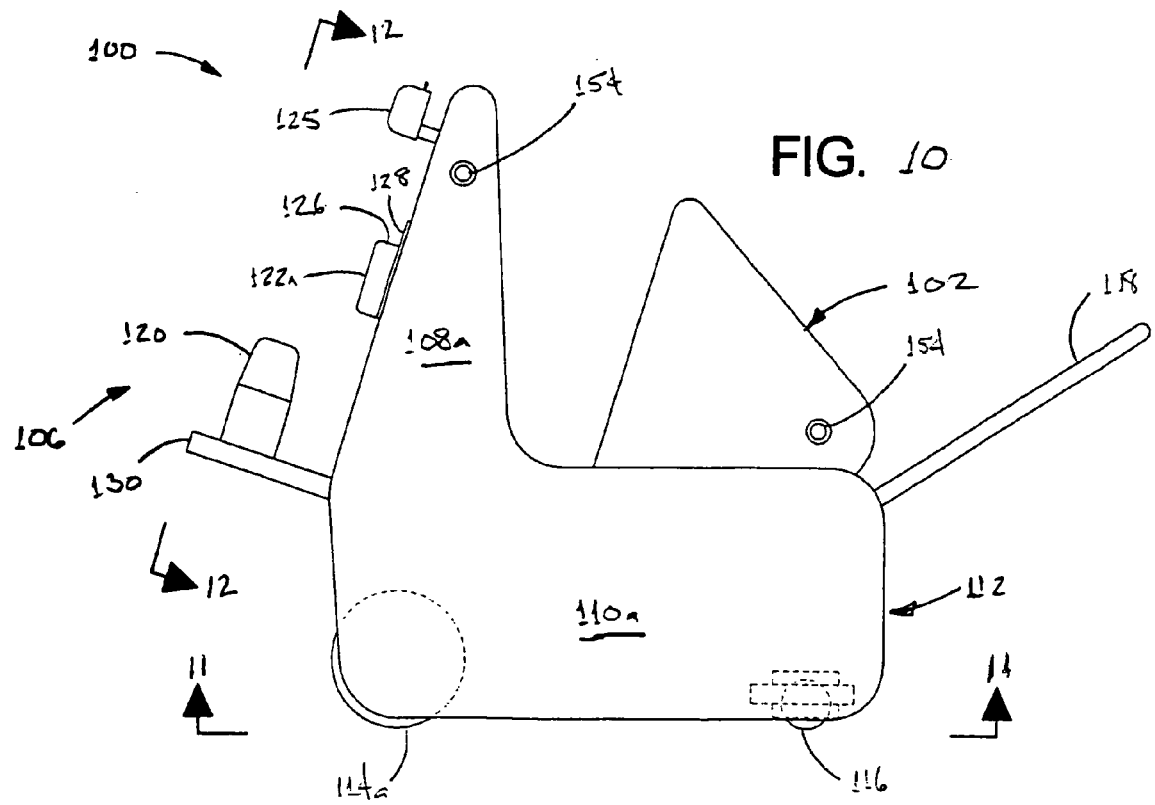

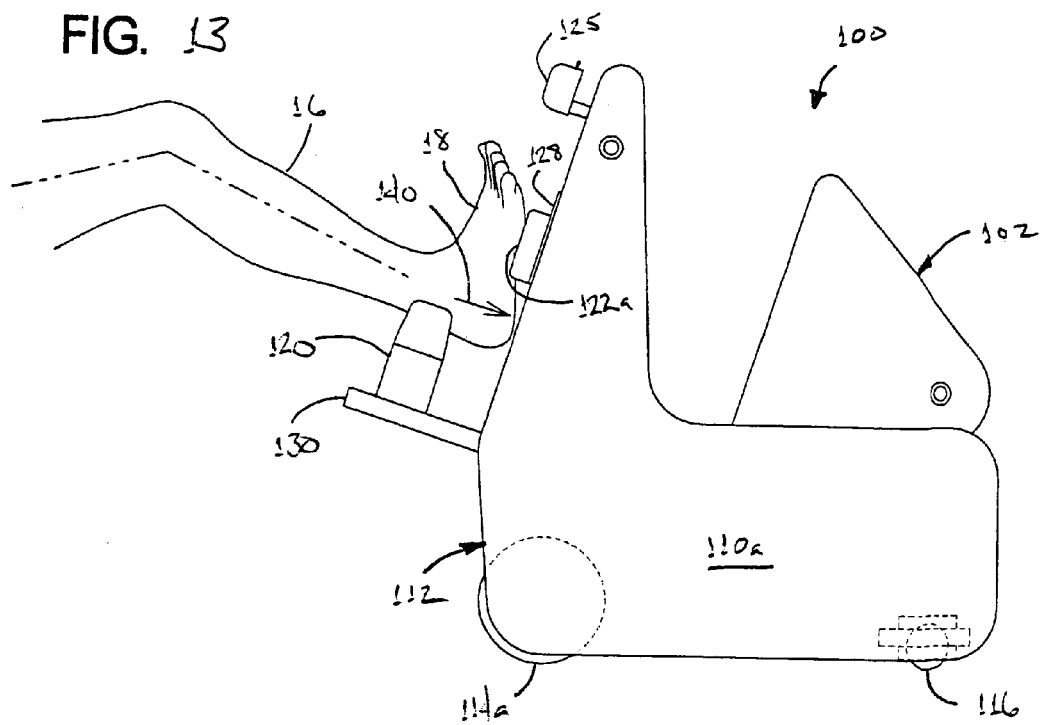
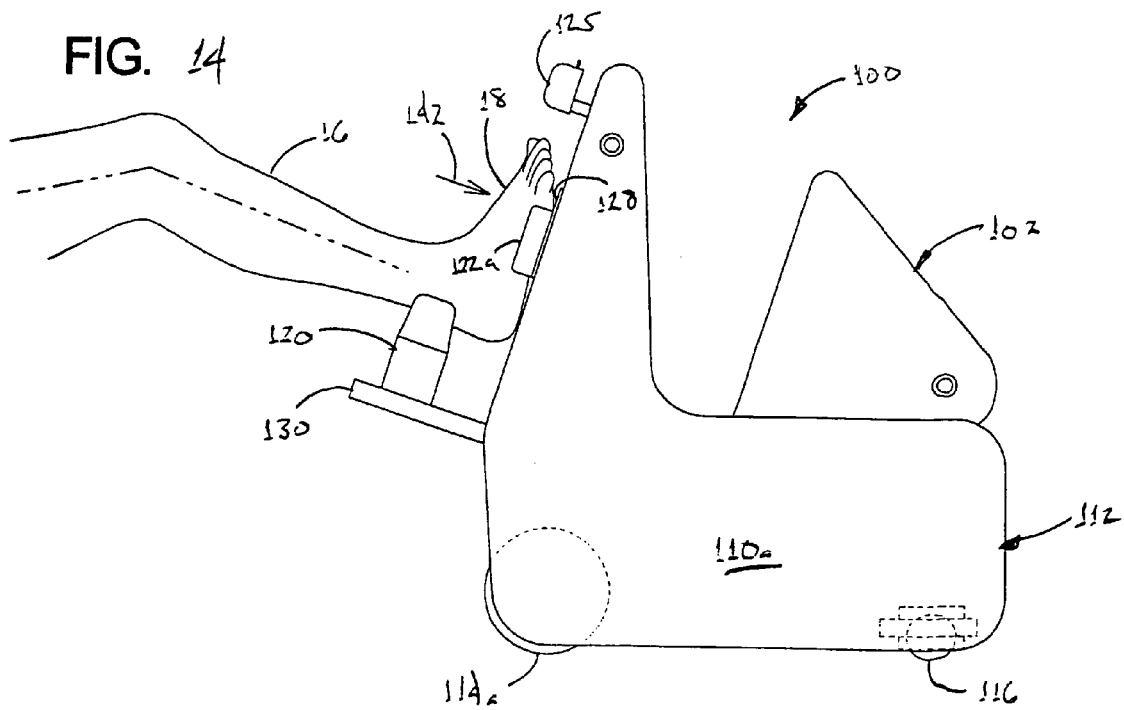

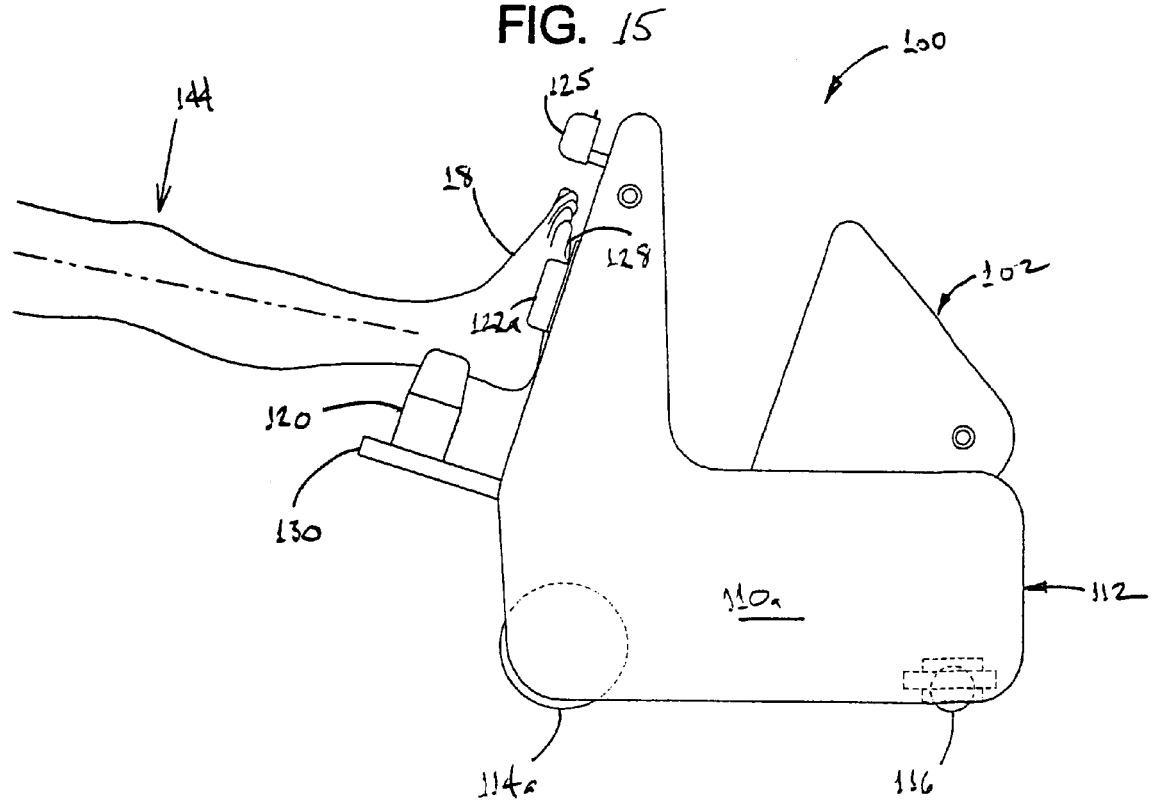

APPARATUS AND METHOD FOR IMAGING FEET

RELATED CASES

This application claims the priority of Provisional Application No. 61/402,601 filed on Aug. 31, 2010.

BACKGROUND a. Field of the Invention

The present invention relates generally to apparatus and methods for obtaining measurements of human feet, and, more particularly, to an apparatus and method for obtaining measurements of the contours of human feet with the feet held in a preferred physical configuration, for use in the manufacture of orthotic devices or for other purposes.

b. Related Art

Obtaining accurate measurements of the human foot, and more particularly an accurate determination of its shape and contours, is desirable for many purposes. Perhaps the most basic reason is for the sizing and fitting of shoes, but beyond this are more particular purposes such as for constructing specialized shoe inserts and other orthotic devices. In general terms, the purpose of such orthotic devices is to optimize functions of the foot and/or to correct functional problems that result from deficiencies in the bone structure and/or associated soft tissues of the foot.

Although in many cases substantial benefits can be achieved using inserts and other orthotic devices constructed on the basis of one or more standardized or idealized models of feet, the characteristics of feet naturally vary from person to person, so that in general the maximum benefits can only be provided by a custom-fitted device. This is particularly true in the case of individual feet that differ significantly from the "norm" in terms of shape, structure and/or functional abnormalies. The construction of custom orthotics and similar devices in turn depends on obtaining an accurate representation of the person's foot and of the plantar (lower) surface of the foot in particular.

One traditional technique for obtaining a representation of a patient's foot has been to obtain a direct mold of the foot. For example, the foot may be placed in or covered with a material (e.g., plaster- or resin-laden cloth) that hardens to maintain its shape, in order to obtain a negative mold of the foot. The mold is subsequently filled with plaster or other hardenable material to form a positive representation of the foot, over which the orthotic device is then molded, with corrections being made to the shape of the cast as appropriate.

Although the traditional cast-molding system described in the preceding paragraph can yield excellent results, it is by nature highly labor intensive and time-consuming in practice; furthermore, the process of applying the material to the patient's foot and allowing it to take a set while holding the foot in position requires a minimum of several minutes to complete, during which the foot must be kept essentially immobile, causing inconvenience and potential discomfort to the patient as well as being fatiguing for the clinician. Moreover, common practice is for the molds of the patient's feet to be obtained by podiatrists and other practitioners in various locales and then sent to a specialist laboratory for actual manufacture of the orthotic devices, resulting in significant delays as well as shipping costs.

An alternative to forming a mold directly from the foot is to reduce the shape/contour of the foot to some form of data that can be transmitted to the laboratory for construction of the orthotic device. In some instances, this has been done by using one or more probes or other members that physically contact the foot at a series of locations to determine its contours; for example, certain devices have utilized an array of pin-like probes that are displaced when pressed against the plantar surface of the foot (or vice versa), with various distances by which individual pins/members are displaced representing the contours of the foot.

Other approaches have utilized optics in one manner or another; for example, some systems employ laser scanning mechanisms, with the location of points along the plantar surface of the foot being calculated from an angular relationship between the laser and or other sensor, while other systems project a pattern of lines or other geometric images onto the plantar surface from which the contours can be calculated; with currently available technology, a complete laser scan of the plantar surface of the foot requires only about fifteen seconds to complete, while digital imaging of the foot using projected lines requires a mere fraction of a second. The resulting data, typically digital, can then be conveniently transmitted to the laboratory for manufacture of orthotic devices, for example using a computer-controlled milling machine to form positive casts for molding of the orthotics, or even to form the orthotics themselves.

Systems that are able to produce digitized data accurately representing the contours of the foot, such as those noted above, offer significant advantages in terms of speed, efficiency, economy and patient comfort. However, despite these advantages such systems have on whole failed to provide entirely satisfactory results in terms of the end product, especially by comparison to the traditional molding process. One of the principal reasons, the inventor has found, is that in general such systems have necessarily imparted a degree of distortion to the foot during operation: For example, many prior optical scanners and imagers involve the patients standing on or otherwise placing their feet against a panel of glass or other transparent material, via which the plantar surfaces are exposed to the light source/sensor; pressing the foot against the panel causes the soft tissues of the foot to flatten and spread out in the areas of contact, so that when imaged the surface may be in a configuration that is far from optimal in terms of the function and comfort of the foot.

In addition to distortion of the soft tissues, a serious but somewhat more subtle problem relates to positioning of the bone structure of the foot. As is known to those skilled in the relevant art, the bone structure of the human foot transitions through a series of phases between heel strike and toe off, over what is referred to as the "gait cycle." In particular the foot transitions from an adaptive phase at heel strike, in which the bone structure is comparatively yielding and is able to collapse somewhat to absorb impact and conform to the underlying surface, to a "rigid lever" phase, as weight begins to be transferred onto the forefoot, in which the bone structure becomes more-or-less locked so that the foot can provide stability and effective propulsion at toe off. The correct "locking" of the bone structure, and more particularly of the midtarsal joint, is critical for the foot to function properly, and is therefore a central goal of functional orthotic devices. Accurately configuring an orthotic device to meet this goal, however, requires being able to ascertain the contours of the foot with the bone structure in the correct end-point condition, specifically with the subtalar joint of the foot in what is referred to as the "neutral position" and with the midtarsal joint locked, which is generally difficult or even impossible to accomplish using prior systems such as those noted above. The matter is greatly complicated by the fact that individual feet vary greatly in terms of overall orientation (e.g., in the amount of pronation) when the joints of the foot are in the correct condition.

Accordingly, there exists a need for an apparatus and method for obtaining data representing contours of a foot, accurately and without distortion of the soft tissues or bone structure of the foot. Moreover, there exists a need for such an apparatus and method that is able to obtain the data representing the contours of the foot with the structure of the foot being held in the predetermined correct condition. Still further, there exists a need for such an apparatus and method that can be employed simply, efficiently and effectively in a clinical environment, and that in use is also convenient and comfortable for the patient.

SUMMARY OF THE INVENTION

The present invention addresses the problems cited above, and provides an apparatus for determining contours of the plantar surfaces of a patient's foot, with the foot optimally positioned and configured and without distortion of the soft tissues or bone structure of the foot.

In a broad sense, the apparatus comprises (a) an imaging section that optically measures the contours of the plantar surface of the foot; (b) an alignment section that orientates the foot relative to the imaging section, the alignment section comprising at least one support member that engages the plantar surface of the foot substantially only beneath a lateral forefoot area of the foot, with the plantar surface of the foot directed towards the imaging section; and (c) means for moving the foot relative to the alignment section so that the lateral metatarsal head area of the foot is reactively loaded in a dorsal direction by the at least one adjustable support member so as to lock the midtarsal joint.

The at least one support member may comprise at least one support member for engaging the plantar surface of the foot substantially only beneath an area of the fourth and fifth metatarsal heads of the foot, and preferably may comprise a support member for engaging the plantar surface of the foot substantially only beneath the fifth metatarsal head of the foot.

The at least one support member may further comprise a substantially transparent pad portion that engages the plantar surface of the foot, so that the engaged area of the foot is exposed through the transparent pad to an optical sensor of the imaging section. The at least one support member may be linearly adjustable to accommodate feet having different lengths, and laterally adjustable to accommodate feet having different widths.

The at least one support member may comprise first and second support members mounted on right and left sides of an imaging area of the imaging section of the apparatus. The imaging area may be located proximate a predetermined focal length of the imaging section, so that when a foot is supported on one of the first or second support members the plantar surface of the foot will be located proximate the focal length of the imaging section.

The alignment section of the apparatus may further comprise a heel rest for centering the rearfoot and also the distal aspect of the leg relative to the imaging section of the apparatus. The heel rest may comprise a generally V-shaped heel stirrup. The heel stirrup may be adjustably mounted so as to accommodate feet and legs of different lengths.

The alignment section of the apparatus may further comprise a laser pointer located at the distal aspect of the patient's foot that generates a reference beam for alignment of the patient's foot in the alignment section. The reference beam may be aligned from the laser pointer to a center of the heel rest of the apparatus. The beam may be centered over a viewing area for the imaging section of the apparatus.

The apparatus may further comprise a wheeled carriage for rolling away from the patient in response to pressure exerted in a distal direction by a foot resting in the apparatus. The wheeled carriage may comprise means for allowing the carriage to be freely moveable over a floor in the transverse plane. The means for allowing the carriage to be moveable in the transverse plane may comprise one or more casters mounted on the carriage, or one or more ball transfer units.

The invention also provides a method for determining the contours of the plantar surface of a patient's foot. In a broad aspect, the method comprises the steps of: (a) providing a support proximate an imaging device for determining contours of the plantar surface of the foot; (b) moving the support relative to the foot so as to apply a dorsally-directed reactive force substantially only to a lateral forefoot area of the foot so as to lock a midtarsal joint of the foot; and (c) aligning the foot so that a subtalar joint of the foot is substantially in its neutral condition.

The step of moving the support relative to the foot may comprise moving the support relative to the foot so as to apply a dorsally-directed reactive force to substantially only an area of a fourth and fifth metatarsal head of the foot, preferably to substantially only an area of a fifth metatarsal head of the foot.

The step of applying the reactive force in the dorsal direction may comprise placing the foot into the heel rest with the forefoot dorsiflexed, and then plantarflexing the forefoot onto the support member so that the support member engages the lateral forefoot area so as to generate the dorsally-directed reactive force. The step of plantarflexing the foot may comprise lowering the associated knee into extension and allowing the ankle to plantarflex the foot, preferably to a position in which the foot extends at an angle of about 90° to the ankle.

The step of aligning the foot may further comprise the step of positioning the foot substantially in alignment with a central plane of a viewing area of the imaging section of the apparatus. The step of positioning the foot substantially in alignment with the central plane of the viewing area of the imaging section may comprise the steps of providing a visual reference line that is substantially in alignment with the central plane of the viewing area, and aligning the second metatarsal head area of the foot and the distal one-third of the lower leg with the visual reference line. The visual reference line may be aligned substantially with a center of the heel stirrup of the alignment section. The step of providing a visual reference line may comprise providing a visible beam from a laser pointer device.

The step of aligning the foot so that the subtalar joint is substantially in a neutral condition may comprise aligning the second metatarsal head of the foot with the distal one-third of the lower leg so as to place the subtalar joint of the foot in the neutral position. The step of aligning the second metatarsal head with the distal one-third of the lower leg may comprise placing a rearfoot portion of the foot in engagement with the imaging device, and adjusting a forefoot portion of the foot relative to the rearfoot portion so as to bring the second metatarsal head into alignment with the distal one-third of the lower leg. The step of adjusting the forefoot portion of the foot relative to the rearfoot portion so as to bring the second metatarsal head into alignment with the distal one-third of the lower leg may comprise extending the patient's leg from a bent configuration in which a knee thereof is raised to a straightened configuration in which the knee is lowered, so as to move the imaging device distally and medially relative to the patient to a position in which the device is in coalignment with the second metatarsal head and the distal one-third of the lower leg.

These and other features and advantages of the present invention will be more fully understood and appreciated from a reading of the following detailed description with reference to the accompanying drawings.

BRIEF DESCRIPTION OF THE DRAWINGS

FIG. 9 is a perspective view of a foot imaging apparatus in accordance with another preferred embodiment of the present invention;

FIG. 10 is a side elevational view of the foot imaging apparatus of FIG. 9, showing the configuration and locations of the components thereof in greater detail;

FIGS. 13-15 are sequential elevational, environmental views of the imaging apparatus of FIGS. 9-10 with a patient's foot placed therein, showing the manner in which the foot is set in the alignment section of the apparatus and the leg then extended and the ankle joint plantarflexed, similar to FIGS. 6-8;

DETAILED DESCRIPTION

Figure 1:
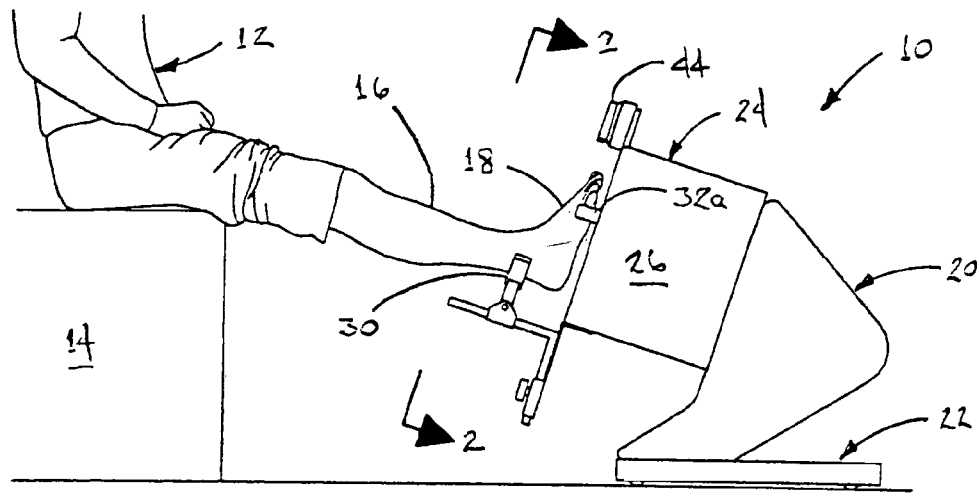
FIG. 1 is a side elevational, environmental view of a foot imaging apparatus in accordance with a preferred embodiment of the present invention, showing the apparatus with the right foot of a patient in position for imaging and measurement of the contours of the plantar surface.

FIG. 1 shows a foot imaging apparatus 10 in accordance with a first preferred embodiment of the present invention. The apparatus is shown in use in conjunction with a patient 12 in a seated position on a chair 14 or other support, with a leg 16 and foot 18 outstretched.

Figure 6:
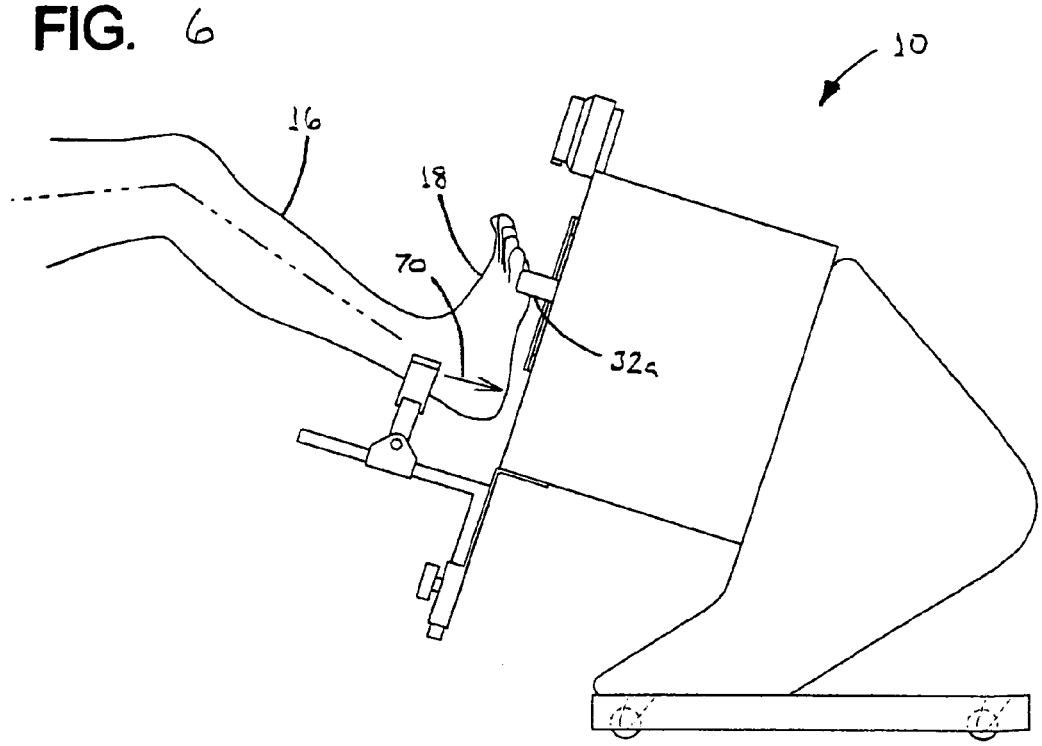
FIGS. 6-8 are sequential side elevational, environmental views of the foot imaging apparatus of FIGS. 1-3, showing the manner in which a patient's foot is placed in the heel support portion of the apparatus with the knee first raised and the ankle dorsiflexed, and the leg then straightened and the ankle plantarflexed.
Figure 7:
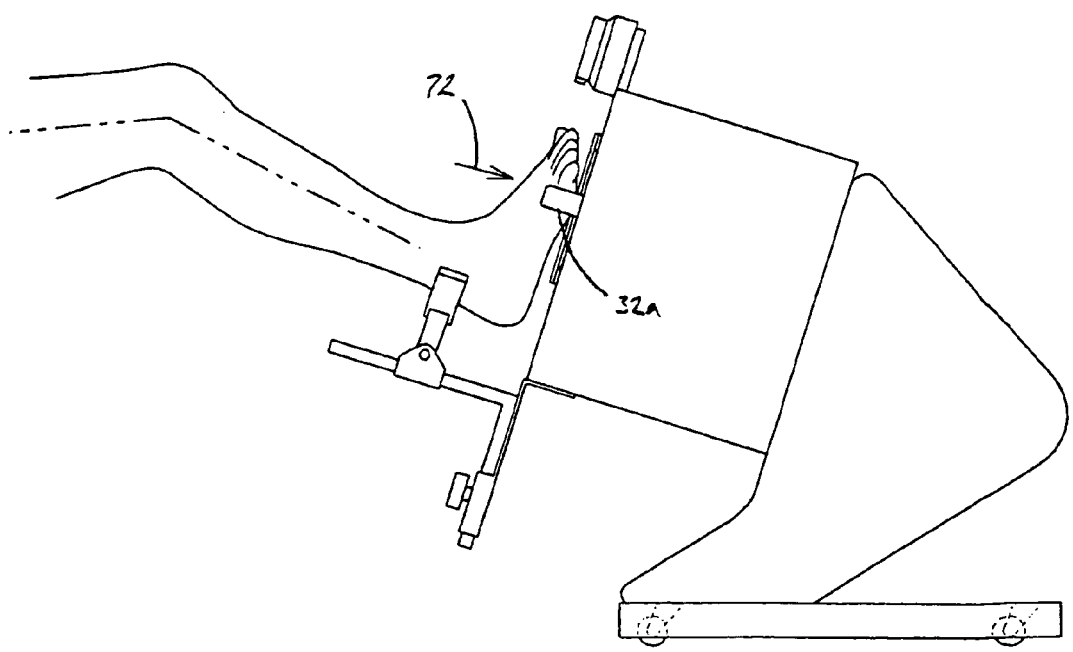
Figure 8:
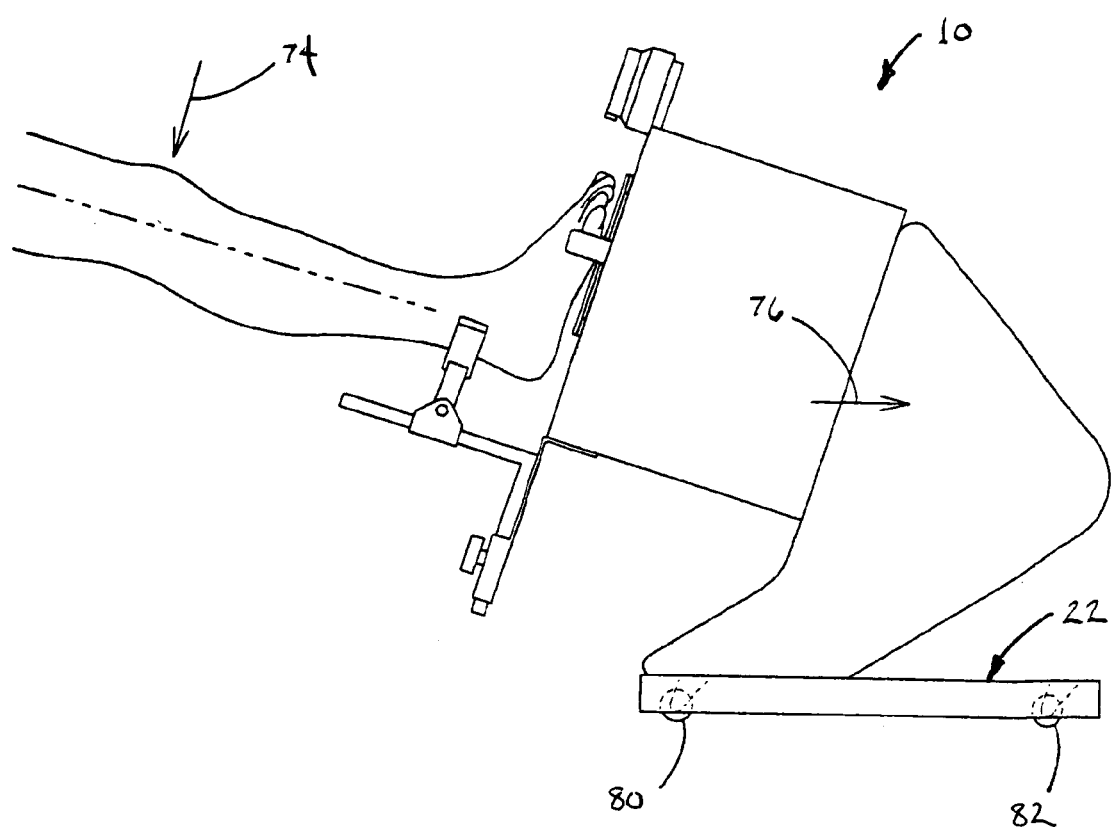

As can be seen with further reference to FIG. 1, the imaging apparatus 10 includes an optical imaging section 20 mounted on a rolling chassis section 22, and an alignment section 24 that is spaced from the imaging section 20 towards the patient's foot 18. The alignment section 24 in the illustrated embodiment includes a spacer frame 26, which in the embodiment illustrated in FIG. 6-7 is formed by a somewhat box-shaped structure, with a through passage and open ends that define an aperture 28 via which the plantar surface of the foot is exposed to the optics of the imaging section 20. A principal function of the spacer frame is to support the alignment components, as described below, such that the plantar surface of the patient's foot will be held proximate a predetermined focal length of the camera in the imaging section 20; it will therefore be understood that the shape and construction of the spacer frame are somewhat arbitrary and may vary significantly depending on design factors.

Figure 2:
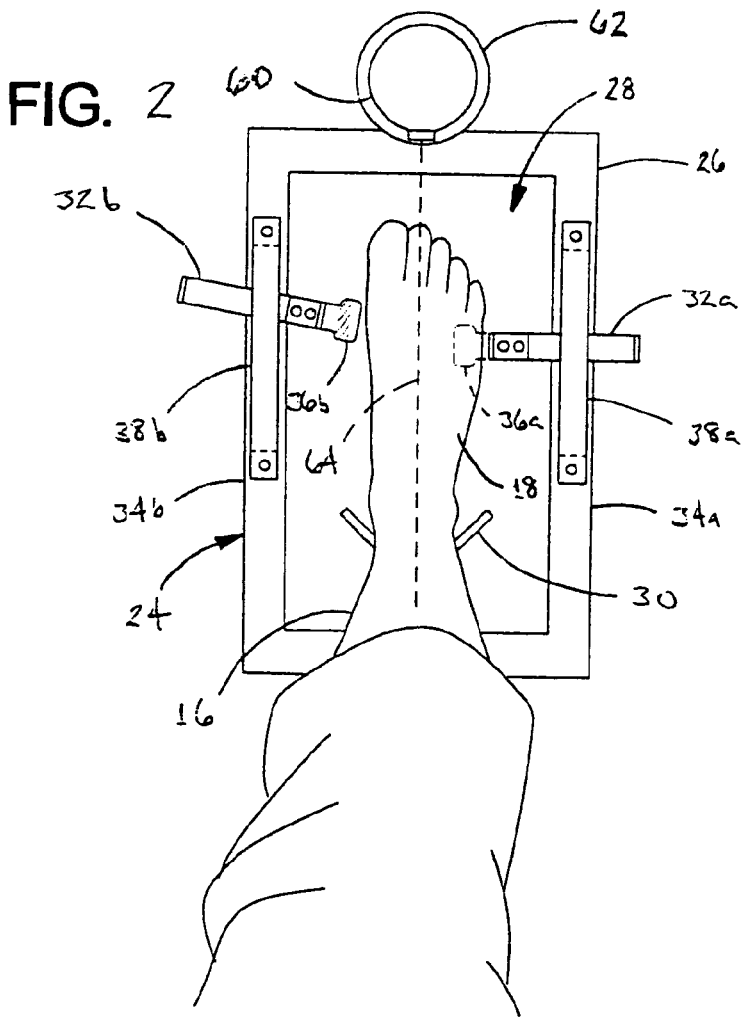
FIG. 2 is a front elevational, environmental view of the foot imaging apparatus of FIG. 1, showing the manner in which the foot is aligned with a laser pointer and also reactively loaded by a support under the fifth metatarsal head so that the foot is held in the correct condition and orientation for imaging.

As can be seen referring again to FIG. 1 and also FIG. 2, the alignment section 24 includes a set of cooperating foot alignment components that are mounted to the outer end of the spacer frame (i.e., the end facing towards the patient), namely, a heel stirrup 30, right and left adjustable supports 32a, 32b for engaging the plantar surface of the foot, and a laser pointer 44 for projecting a visual reference line onto the foot. As will be described in greater detail below, the alignment components serve to position and load the foot such that the bone structure is held steady with the subtalar joint in the "neutral" position and with the midtarsal joint locked, which as explained above is critical for properly determining contours of the foot needed to construct an effective orthotic device. As noted above, the bone structure of a functional human foot transitions through a series of phases beginning with heel strike (when the heel makes initial contact with the ground or other surface), with the bone structure initially being somewhat loose and free to collapse and spread to a degree in order to absorb shock and conform to the underlying surface. Then as weight moves forwardly on the foot, with forward motion of the body, the bone structure transitions to a comparatively rigid configuration: In particular the center of weight, as borne by the plantar surface of the foot, initially follows a somewhat forward and lateral path, as the rearfoot simultaneously undergoes eversion, with the midtarsal joint becoming "locked" as the center of weight transfers onto the area of the fifth metatarsal head (generally in the area beneath the base of the small toe). The midtarsal joint remains locked for the remainder of the gait cycle, so that the foot forms a substantially rigid "lever" for efficiently transmitting force to the ground during toe-off. A more complete explanation of the gait cycle and the locking and unlocking of the metatarsal joint is found in U.S. Pat. No. 5,960,566, which is incorporated herein by reference.

The alignment components of the present invention exploit the characteristics of the foot as a rigid lever, as described in the preceding paragraph, to locate the foot in position for imaging of its plantar surface; moreover, in the present invention this is accomplished without distorting the soft tissue or bone structure of the foot.

As can be seen in FIGS. 1-2, the heel rest or "stirrup" 30 is preferably somewhat V-shaped so as to have a centering effect on the rearfoot, and therefore also the distal portion of the leg, and is spaced somewhat away from the general plane of the plantar surface, the latter being located proximate aperture 28, so as to retainingly engage the foot in the area located near the top of the heel area/bottom of the distal one-third of the lower leg, with the size and angle of the V-shaped area being configured to hold this area of the leg firmly but without discomfort to the patient. The V-shaped stirrup 30 is generally located along the centerline of the aperture 28 and therefore along the axis of the imaging section, thus allowing it to be used with either right or left feet.

Figure 3:
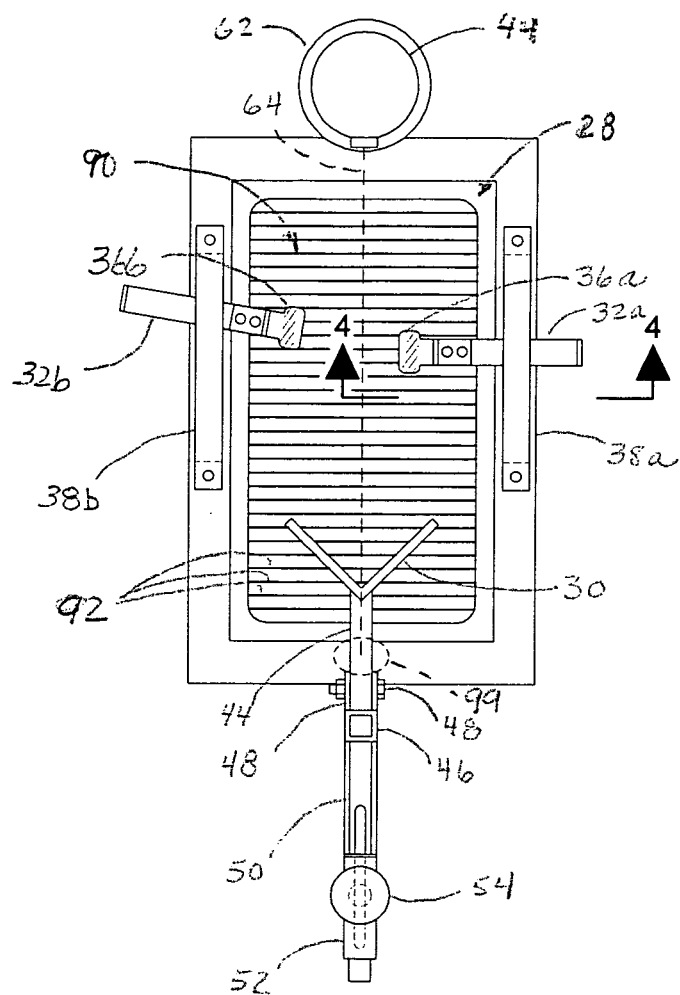
FIG. 3 is a front elevational view of the apparatus of FIGS. 1-2, with the patient's foot removed, showing the supporting structure and also the face of the optical imaging section of the apparatus.
Figure 4:
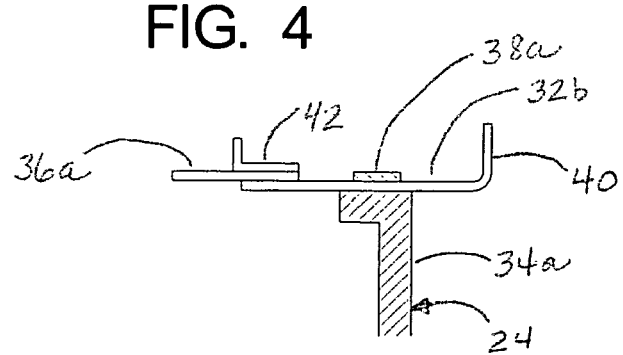
FIG. 4 is a partial cross-sectional view of the foot imaging apparatus of FIGS. 1-3, taken along line 4-4 in FIG. 3, showing the structure of the adjustable support in greater detail.

As can be seen with further reference to FIG. 2 and also FIGS. 3-4, the right and left adjustable support members 32a, 32b project inwardly towards the centerline of the aperture 28 from respective sidewalls 34a, 34b of the spacer frame 24. Pad members 36a, 36b are mounted on the inboard ends of the adjustable arms 32a, 32b, and are preferably formed of a rigid yet transparent material that is capable of applying a dorsally-directed force to the plantar surface of the foot without obscuring it from view by the imaging section, such as plexiglass or Lexan™ for example. The pad members 36a, 36b are preferably sized to engage only the area of the foot immediately beneath the fifth metatarsal head, with dimensions of about 1" by 0.5" being generally suitable.

The arm members 32a, 32b are adjustable to accommodate different lengths and widths of feet; in the embodiment that is illustrated in FIGS. 1-4, the arm members 32a, 32b are held in sliding engagement against the end surfaces of the sidewalls 34a, 34b of the spacer frame 24, by guide strips 38a, 38b that are secured to the end surfaces so as to define slots sized to form a friction-fit but slidable engagement with the respective arm members. The arm members can therefore be selectively slid both longitudinally and laterally (in and out) with respect to the centerline of the aperture 28, so as to position the pads 36a, 36b beneath the fifth metatarsal head area of feet having different sizes, the right side arm and pad being used for right feet and the left side arm and pad being used for left feet. As can be best seen in FIG. 4, the arm members are preferably provided with upturned tab portions 40 on their outer ends that facilitate manual adjustment of the arm members, as well as upturned end plates 42 located at the junctions where the transparent end pads are mounted to the arm members, the latter serving to engage the sides of the foot lateral of the transparent pads so that only the transparent material extends below the plantar surface of the feet.

The position of the heel stirrup 30 is also adjustable to accommodate feet and legs of different sizes. First, as can be seen in FIG. 3, the stirrup is supported on the upper end of a generally vertical arm 44 that is joined to a second, horizontal bar by a bracket 48 that is in frictional engagement with the latter. The heel stirrup can therefore be selectively slid towards and away from the support arms 32a, 32b at aperture 28, as indicated by arrow 49 in FIG. 5, to accommodate feet having smaller/shorter or bigger/taller rearfoot areas and/or difference in the size of the distal one-third of the lower leg. The end of horizontal bar 46 is mounted to a second, generally vertical bar 50, that passes through a friction-fit sleeve 52 in sliding engagement therewith, the sleeve being fixedly mounted to the spacer frame 24 by a bracket 56; friction through the sleeve 52 is controlled by a knob 54, so that the position of the stirrup is adjustable in a generally vertical direction as indicated by arrow 58 in FIG. 5.

Also mounted at the end of the spacer frame 24 proximate aperture 28 is the laser pointer 60, held in place by a support bracket 62, that projects a visible beam 64 generally along the centerline of the aperture 28 and also in alignment with the center of the V-shaped heel stirrup 30 as well as the central plane of the camera 98, as indicated by the dotted-line image in FIG. 3. The laser beam thus provides a visual reference line for the center plane of the aperture 28 and the imaging area as a whole.

As was noted above, the components of the alignment section serve to orientate the bone structure of the foot with the midtarsal joint in the locked position, employing alignment of the bone structure in conjunction with a dorsally-directed (upward) loading of the fifth metatarsal head, essentially mimicking the reactive force of gravity experienced by the fifth metatarsal head at the corresponding point in the gait cycle.

The steps in accomplishing the positioning and locking of the foot are best seen in FIGS. 2 and 6-8. As an initial step, the imaging apparatus 10 is brought into proximity with the seated patient, so that the centerline that is established by the laser pointer and V-shaped heel stirrup is in general alignment with and towards the user's hip on the side of the foot that is to be imaged (e.g., in general alignment with the right portion of the hip if the right foot is to be imaged). The patient's foot is then placed in the stirrup 30 as shown in FIG. 6, with the knee slightly bent (raised), and with the ankle dorsiflexed and the heel thrust forward as indicated by arrow 70 in FIG. 6, so that the plantar surface of the heel is located closely proximate the plane that is defined by the adjustable pads 36a, 36b at aperture 28. In so doing, the stirrup takes the majority of the weight off of the extremity, which simultaneously centralizing the rearfoot and distal one-third of the lower leg relative to the aperture and imaging section. The clinician (operator) adjusts the respective arm member 32a, 32b so that the associated pad 36a, 36b is positioned beneath the lateral forefoot, and in particular the fifth metatarsal head of the bone structure as shown in FIG. 2, and the patient then plantarflexes the ankle joint so as to lower the forefoot as indicated by arrow 72 in FIG. 7. In so doing, the plantar surface of the forefoot in the area beneath the fifth metatarsal head comes into contact with the pad 36a/36b on the support arm, so that the fifth metatarsal head is held against further movement in the plantar direction; plantarflexing the forefoot merely requires the patient to relax the ankle from holding the foot from the "heel forward" condition in which the foot is initially set in the stirrup, so that when the forefoot is fully relaxed and lowered, the fifth metatarsal head is subject to an upward (dorsally-directed) force mimicking the loading of the fifth metatarsal head created by the force of gravity during the corresponding phase of the natural gait cycle. A dorsally-directed force sufficient to load the fifth metatarsal head to resistance is created merely by the tension exerted by the muscles of the lower leg when in a relaxed condition, acting through the Achilles tendon and with the ankle joint serving as the fulcrum, so that the midtarsal joint assumes the locked configuration without the patient having to purposely press down on the forefoot using the muscles and ligaments in a manner that might cause distortion of the foot or deviation from the correct shape, and without the area of the fifth metatarsal head having to bear excessive weight that might also cause distortion of the tissues and/or patient discomfort.

To centralize the foot relative to the central axis of the viewing area and place the subtalar joint in a neutral condition, while keeping the midtarsal joint locked, the leg is next adjusted to position the second metatarsal head (in the area proximate the base of the second toe) with the beam 64 that is projected by the laser pointer 44, the beam being aligned with the center of the heel stirrup as noted above; in the embodiment of FIGS. 1-8, centralization of the foot is achieved by sliding the adjustable arm members 32a, 32b in or out as necessary. The patient's knee is then lowered and the ankle joint concurrently plantarflexed to about 90°, as indicated by arrow 74 in FIG. 8, so as to push the apparatus 10 away from the chair or other support on which the patient is seated. In response, the apparatus rolls away from the patient over the floor on its wheeled chassis, as indicated by arrow 76 in FIG. 8; wheeled chassis 22 is supported by a pair of casters 80 at its trailing end (toward the patient) and a single caster 82 at its leading end (away from the patient), so as to permit the chassis to turn inwardly in an arc towards a patient's centerline as the apparatus moves away from the patient, thus accommodating the natural inward deviation (angle towards the midline of the body) that is present in most lower legs. The effect of the combined distal and medial motion of the apparatus is to bring the second metatarsal head of the foot into general alignment with the distal one-third of the lower leg so as to place the subtalar joint in the neutral condition, with the alignment being verified visually by the line of the laser beam pausing over the top of the second metatarsal head and up the distal portion of the lower leg. In practice, it has been found that with casters and a floor surface selected for minimal rolling resistance, the inward turning action of the cart as it rolls away from the patient very effectively obtains the correct alignment of the foot to the leg (as shown in FIG. 2) with little or no intervention or subsequent adjustment being required by the clinician; to the extent that minor corrections or "fine tuning" of the alignment is needed, this is easily performed by simply sliding the support arms in or out in the manner described above, to bring the second metatarsal head and lower third of the lower leg back into alignment with the beam of the laser.

It will be understood that other arrangements of casters or wheels may be used on the cart to allow the rolling and turning action, in addition to the "tricycle" caster arrangement described, and furthermore that in some instances the patient may be seated on a chair or other support that rolls away from and/or turns relative to the imaging apparatus rather than vice versa.

Positioned and locked in the manner described, the pad 36a/36b on which the fifth metatarsal head rests effectively establishes the transverse plane of the foot, at a position proximate the focal length of the camera of the imaging section of the apparatus. Since, in the illustrated embodiment, the V-shaped heel stirrup holds the rearfoot and distal one-third of the lower leg essentially perpendicular to the plane of the metatarsal support pads 36a, 36b, the two pads effectively establish a transverse plane of the foot at essentially 0° eversion/inversion relative to the frontal plane. However, as noted above, individual feet vary greatly, and depending on the degree of eversion exhibited by the foot (e.g., 6° everted, 8° everted, and so on), the medial aspect of the forefoot may in some instances be positioned above the 0° transverse plane or below the 0° transverse plane when the midtarsal joint is locked and the subtalar joint is in the neutral position. Therefore, another significant advantage of the present invention, in which a support exists only under the lateral forefoot and preferably only under the fifth metatarsal head rather than all the way across the foot, is that the medial aspect of the foot is free to elevate above or depress beyond the 0° transverse plane as the nature of the particular foot dictates, which is not possible in the case of devices in which the entire width of the foot is pressed against a plate of glass or other continuous support or surface.

With the foot aligned and held in the manner described, the entire plantar surface of the foot is exposed to the optical system of the imaging section of the apparatus, the area under the fifth metatarsal head being "visible" to the optics by virtue of the transparent material of which the support pads are formed. Furthermore, since the foot is centered on the central plane of the camera (at aperture 28), the camera is able to capture the image a sufficient distance up both sides (medial and lateral) of the foot, so that adequate contour data can be obtained without need for views at multiple angles or using multiple cameras. In the preferred embodiment that is illustrated in FIGS. 1-5, the imaging section utilizes a three-dimensional measurement instrument that operates on the basis of projecting a pattern of parallel lines onto the plantar surface of the foot and then capturing the resulting image using a camera set at a predetermined angle to the axis of projection, the image then being analyzed to determine the contours of the plantar surface. Such three-dimensional digitizers are available, for example, from Virtual 3-D Technologies Corp., Cutchogue, N.Y., USA, systems of this general type sometimes being referred to as "white light" digitizers. As compared with systems based on scanning lasers, "white light" digitizers offer significant advantages, including almost instantaneous operation and therefore the ability to effectively "freeze" the image of the foot and eliminate the effects of movement, greatly simplifying operation in a clinical environment. It will be understood, however, that in some embodiments other forms of three-dimensional imaging systems may be utilized in the imaging section of the apparatus, including but not limited to scanning laser systems, for example.

Figure 5:
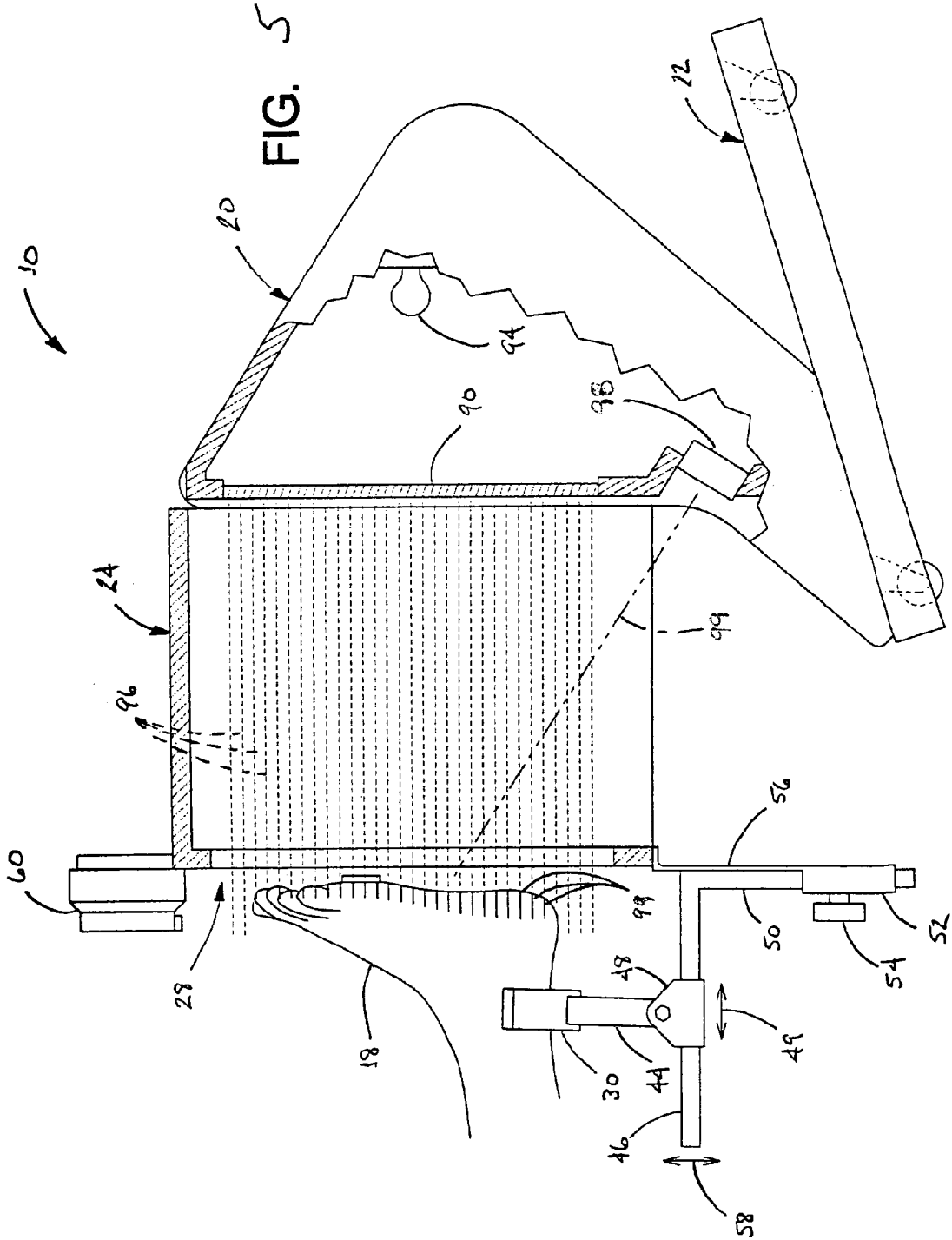
FIG. 5 is an enlarged side elevational view of the imaging apparatus of FIG. 1-3, partially in cutaway, showing the manner in which the optical imaging section of the apparatus projects a pattern of lines onto the plantar surface of the foot, that are viewed at an angle by a camera to determine the contours of the plantar surface.

Inasmuch as the "white light" three-dimensional digitizer alone is a more-or-less "off the shelf" component, its operation will be described herein only briefly. As is shown in FIG. 3, the digitizer employed in the illustrated embodiment includes a transparent or semi-transparent face plate 90 on which a series of opaque, parallel, transverse orientation lines 92 are formed. As can be seen in FIG. 5, a bulb 94 or other light source is positioned in the housing of the digitizer behind the faceplate 90, generally along an axis substantially perpendicular to the plantar surface of the foot 18. Operation of the light source 94 illuminates the plantar surface of the foot, with the images of the opaque lines 92 being projected against the plantar surface, as indicated by dotted lines 96, to create a corresponding pattern of lines 78 on the surface of the foot. The resulting image is captured by a camera 98 set to view the surface along an axis 99 a predetermined acute angle to the axis at which the pattern is projected onto the foot. Thus, although the lines 97 appear generally parallel as viewed along the projection axis from plate 90, the contours of the plantar surface of the foot cause the lines to deviate from parallel in the image that is captured by camera 98. The deviation from parallel, combined with the known angle between the axis of projection and the axis of the camera, and other factors, permits the contours of the foot to be accurately calculated by associated software, with the data being outputted in suitable digital form.

The data representing the contours of the patient's foot can therefore be obtained quickly and conveniently in a clinical environment using the apparatus of the present invention. The patient may be seated in a suitable chair and place his or her foot into the alignment section of the apparatus in the manner described and then push away, with the attendant clinician making minor adjustments as necessary and simply activating the switch to digitize the contours of the foot. Not only are clinical efficiency and patient comfort greatly enhanced, but the opportunities for error are greatly reduced as compared with prior techniques.

FIGS. 9-18 illustrate a second preferred embodiment of the present invention, which is generally similar to the embodiment described above in terms of overall operation and layout, but which differs somewhat in its carriage and alignment sections.

As can be seen in FIG. 9, the apparatus 100 includes an imaging section 102 that is substantially the same as described above and includes a face plate 104 for projecting a pattern of parallel lines onto the plantar surface of the foot. Rather than being supported on a box-like spacer frame, however, the alignment section 106 of the apparatus is supported on a pair of rigid flange portions 108a, 108b that extend upwardly from the sidewalls 110a, 110b of the wheeled chassis 112. Also, rather than the pivoting casters of the embodiment described above, the wheeled chassis includes a pair of horizontal axis wheels 114a, 114b on the trailing end disposed towards the patient, and a single ball transfer unit (ball roller) 116 on the opposite end that is free to roll in any direction; it will be understood that in some instances there may be multiple ball transfer units rather than the single unit that is shown. A particular advantage of the arrangement of wheels and ball transfer unit employed in chassis 112, as compared with conventional casters, is that this avoids the initial pivoting motion or "jog" that is created by the offset vertical axes of casters, which allows the apparatus to follow a comparatively smooth, unbroken arc as it moves away and pivots towards the centerline of the body as the patient's leg is extended, and which also facilitates free movement of the chassis in the transverse plane of the floor in order to perform adjustments as necessary.

Figure 11:
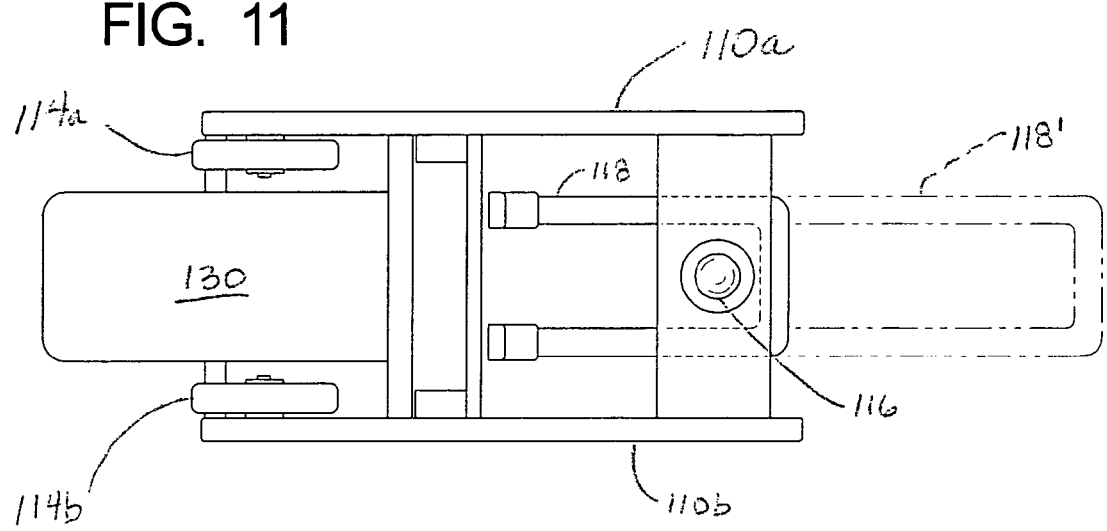
FIG. 11 is a bottom plan view of the apparatus of FIGS. 9-10, taken along line 11-11 in FIG. 10, showing the configuration of the wheeled chassis of the apparatus in greater detail.

As can be seen with further reference to FIG. 10 and also FIG. 11, the chassis 112 includes an optional extensible (e.g., telescoping) handle 118, on the side disposed away from the patient, both to provide an aid to the clinician in adjusting the position of the chassis and also to facilitate transportation of the assembly between locations, such as between examination rooms.

Figure 12:
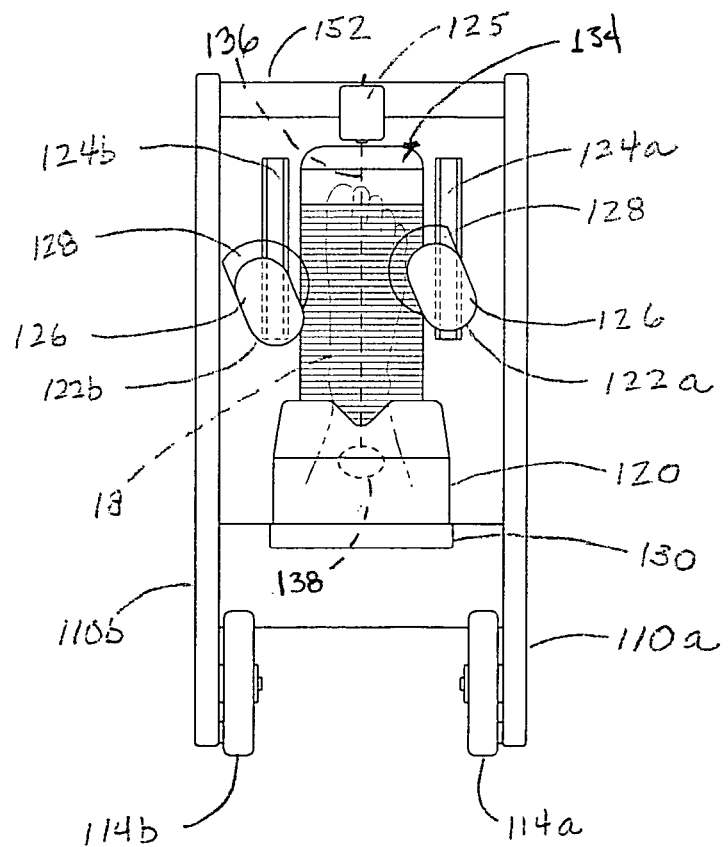
FIG. 12 is a rear elevational view of the apparatus of FIGS. 9-10, taken along line 12-12 in FIG. 10, showing the configuration of the alignment components of the apparatus in greater detail.

Referring again to FIGS. 9-10, it can be seen that the alignment section 106 of the embodiment illustrated therein includes a V-shaped heel stirrup 120, right and left adjustable plantar support members 122a, 122b, and a laser pointer 125, that perform functions similarly to the corresponding elements described above. Rather than sliding bars, however, the adjustable support members 122a, 122b are rotatable units slidingly mounted in generally vertical channels 124a, 124b. As can better be seen in FIG. 12, the rotatable supports include hand grip portions 126, and inwardly disposed somewhat semicircular projecting flange portions 128 formed of a transparent material, similar to the transparent support pads described above. Thus, as can be seen in FIG. 12, the transparent support flanges 128 are positioned beneath fifth metatarsal areas of the feet simply by sliding the respective (right or left) support member 122a, 122b through its associated track to the general location and then rotating the flange inwardly, by turning handgrip 126. As can be seen the handgrips 126 preferably have an enlarged oval form, with the distance between the edge of the handle and the outer edge of the clear projecting flange 128 being selected such that the flange will be positioned beneath the fifth metatarsal head when the handle portion is moved to be adjacent or in contact with the side of the foot. The semicircular shape of the transport flanges 28 in combination with the slide channels, also facilitates rapid and convenient positioning of the supports beneath the heads, so that this can be accomplished without excessive manipulation or "fiddling."

The V-shaped heel stirrup 120, in turn, is supported on a platform 130 that projects towards the patient, in sliding engagement with a pair of tracks 132a, 132b that permit the stirrup to be moved towards or away from the aperture 134 in a manner similar to that described above, but with a simplified sliding motion. The sliding interfit between the tracks and the cooperating portions of the heel stirrup 120 preferably includes a slight frictional resistance, as do tracks 124a, 124b and the cooperating portions of the adjustable members 122a, 122b, so that the members can be conveniently slid to the desired locations but will then remain in place without assistance once released. As with the heel stirrup described above, stirrup 120 is centered on the central plane of the imaging section of the apparatus, as can be seen from its relationship to beam 136 and camera 138 in FIG. 12.

Use of the apparatus 100 and the manner in which it cooperates with a patient's foot and leg is generally similar to the embodiment described above, and is illustrated in FIGS. 13-18.

As can be seen in FIG. 13, the user's foot is first placed in the heel stirrup with the knee raised and the forefoot dorsiflexed and heel pressed forward, as indicated by arrow 140. The respective lateral forefoot support member 122a, 122b is adjusted into position along its track, and then rotated inwardly to move the clear support flange 128 thereof into the area beneath the fifth metatarsal head of the foot. The patient next relaxes the foot and allows the ankle to plantarflex the forefoot, as indicated by arrow 142, so that the fifth metatarsal head is subjected to a mild reactive force in the dorsal direction, mimicking the force of gravity so as to lock the midtarsal joint in the manner described above. The support member 122a/122b is then rotated inwardly/outwardly as needed in order to align the second metatarsal head of the forefoot with the centerline beam 134 projected by laser 125.

Figure 16:
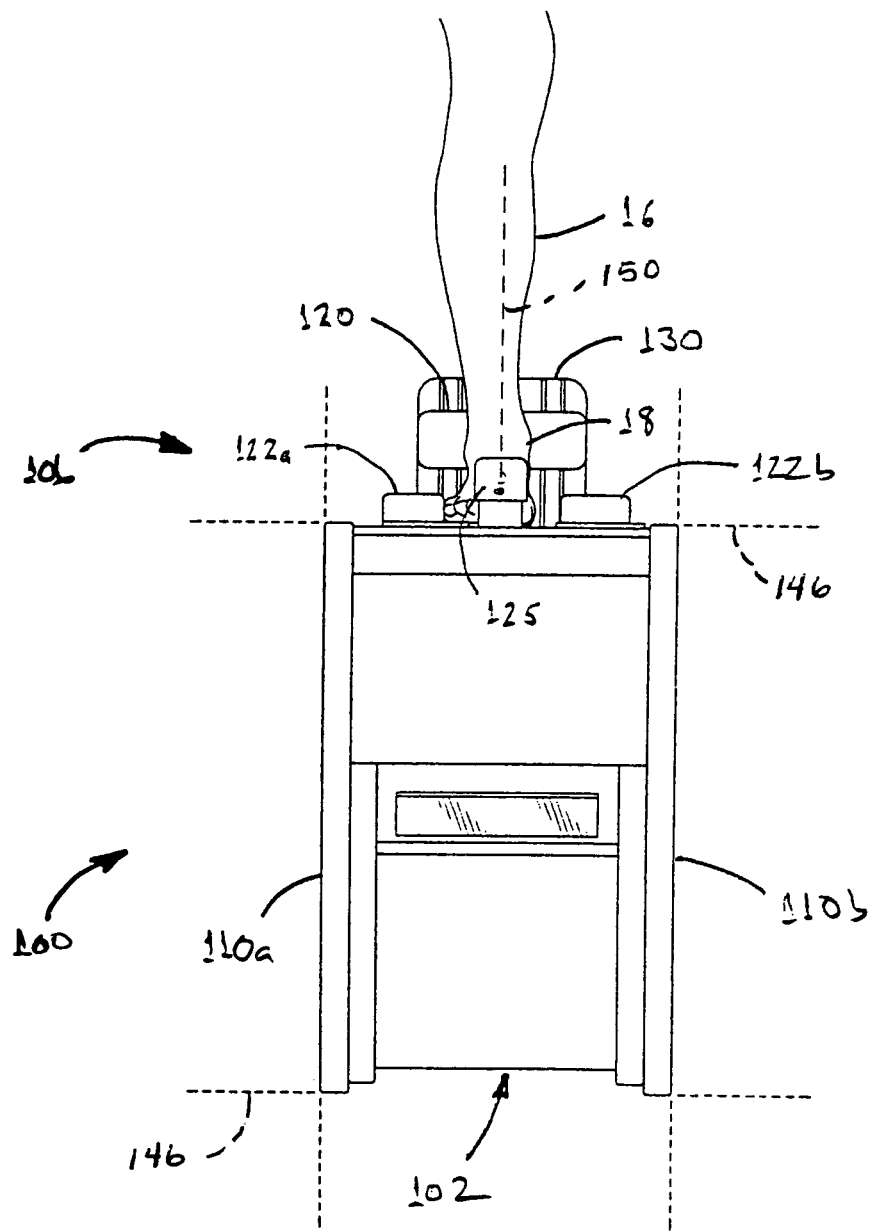
FIG. 16 is a first top plan, environmental view of the apparatus of FIGS. 9-10 with the patient's foot placed therein, in the position shown in FIG. 14 with the leg bent and the knee raised and with the ankle joint dorsiflexed.
Figure 17:
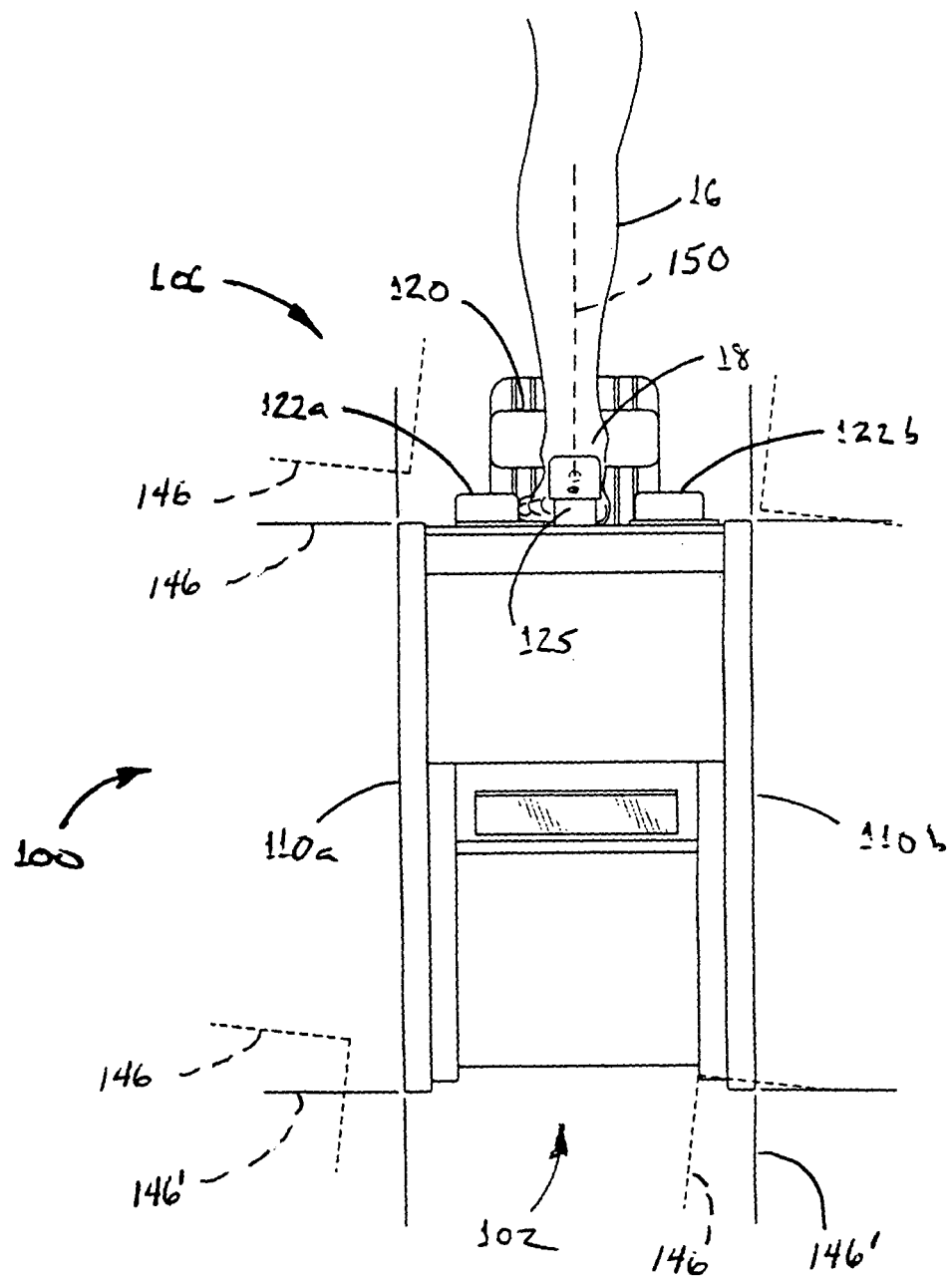
FIG. 17 is a second top plan, environment view of the apparatus of FIGS. 9-10 with the patient's foot placed therein, in the position shown in FIG. 16 with the ankle plantarflexed and the knee lowered and the leg extended so as to push the apparatus away from the patient.
Figure 18:
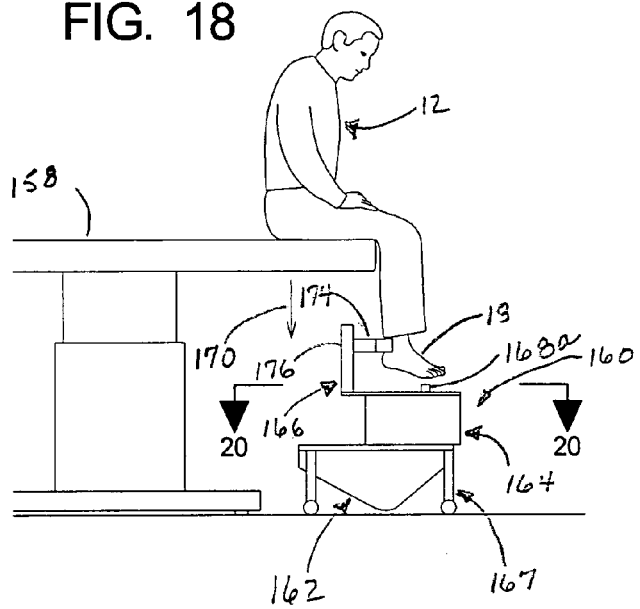
FIG. 18 is a side elevational, environmental view of a foot imaging apparatus in accordance with another embodiment of the present invention, in which the foot is moved vertically relative to the alignment section of the apparatus to reactively load the area of the fifth metatarsal head to lock the midtarsal joint, and the chassis of the apparatus is moved medially/laterally and/or proximally/distally as needed to align the foot and place the subtalar joint in a neutral condtion.
Figure 19:
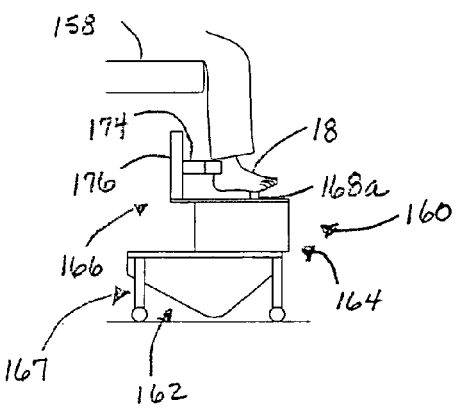
FIG. 19 is a second side elevational, environmental view of the foot imaging apparatus of FIG. 9, showing the position of the foot when it has been lowered onto the alignment section of the apparatus.

The patient then lowers the knee and extends the leg, as indicated by arrow 144 in FIG. 16, causing the apparatus to roll outwardly and turn inwardly (towards the patient's centerline), as can be seen by comparison of FIGS. 17-18. In particular, FIG. 17 shows the orientation of the apparatus 100 relative to the patient when in the position of FIG. 14, i.e., with the forefoot plantarflexed 90° to the lower leg but with the knee still raised; as can be seen therein, the apparatus, including its wheeled chassis at this point, lies in substantially coaxial alignment with the patient's lower leg and the associated side of the hip. However, as the patient lowers the knee and straightens the leg so as to push the apparatus away, the inward deviation of the lower leg causes the leading (distal) end of the apparatus to turn inwardly towards the centerline of the patient's body, as is indicated by the shift between the dotted and solid reference lines 146, 146' in FIGS. 17 and 18, allowing the second metatarsal head and distal one-third of the lower leg to come into alignment with one another and with the beam 150 projected by the laser 125. In short, as the patient pushes the apparatus away the wheeled chassis allows the apparatus, and in particular the central plane of the imaging section, to align itself with the distal one-third of the lower leg such that the subtalar joint is in the neutral position. Minor adjustments can then be made by the clinician if necessary, rotating the handgrip of the associated support and/or using handle 118 and also a crossbar 152 at the top of the alignment section. To move the foot into alignment with the center plane of the imaging section, as indicated by the beam 136 of the laser pointer passing over the second metatarsal head of the foot and onto the distal one-third of the lower leg; in so doing, the neutral position of the subtalar joint can be approximated/verified by the clinician manually rotating the lower leg internally and externally and observing the resultant movement of the laser beam 136, to one side and the other from alignment with the second metatarsal head and distal one-third of the lower leg. The image of the plantar surface of the foot is then captured for digitization by simply pressing one of the switches 154 that actuate the imaging section 102 of the apparatus.

It will be understood that in some cases or embodiments the dorsally-directed load may be applied to the area of the fifth metatarsal head in a direct manner, rather than by first setting the foot into the stirrup or other support with the heel projected and then pantarflexing the forefoot onto the support as described. However, it has been found that such an approach generally leads to the ankle joint being in a plantarflexed position and the remainder of the foot in an inverted position relative to the transverse plane at the viewing area, and therefore less than optimal results when imaged. This problem is avoided by placing the foot/leg on the stirrup with the ankle dorsiflexed and then plantarflexing the foot, in the manner that has been described.

The embodiments described above employ wheeled chassis to achieve relative movement between the patient and alignment section in order to position the foot with the midtarsal joint locked and the subtalar joint in the neutral position. FIGS. 18-22, in turn, illustrate an embodiment in which the patient's foot is lowered onto the support member of the apparatus in order to establish the requisite reactive force acting dorsally on the fifth metatarsal head.

Accordingly, as can be seen in FIG. 18, the patient 12 is seated on a vertically movable platform 158, such as an examination table for example, with the foot 18 positioned more-or-less directly over the apparatus 160. The apparatus 160 includes an imaging section 162 and spacer frame 164 similar to the corresponding components of the embodiment shown in FIGS. 1-2, and also an alignment section 166, all supported on a wheeled chassis 167. However, rather than moving horizontally to load the foot, the assembly remains in position on the floor as the patient is lowered to bring the fifth metatarsal head area of the foot into contact with the adjustable support 168, as indicated by arrow 170 in FIG. 18.

Since relative movement is provided by the table 158 or other vertically moveable support, the patient need not dorsiflex the foot before placing it in the apparatus; instead, the heel is simply positioned in the heel stirrup 174 and reactive force is generated as the fifth metatarsal head area of the foot comes into contact with and is then reactively lifted by the transparent pad 172 at the end of the support member 168a/168b; in so doing, the heel stirrup 174 is allowed to move vertically with the foot by the sliding engagement formed with its upwardly projecting support 176, similar to the stirrup 120 and support 130 described above. The position of the apparatus can then be adjusted in the transverse plane of the floor to place the subtalar joint in the neutral configuration and bring the foot into alignment, with the beam 178 of laser 180 aligned with the second metatarsal head and distal one-third of the lower leg, by moving the apparatus on the floor in the necessary direction or directions using wheeled chassis 167. It will be understood that relative vertical movement between the apparatus and the patient's foot may in some instances be established by raising the apparatus, or an operative portion thereof, relative to the patient's foot, rather than lowering the patient's foot onto the apparatus as shown.

Figure 20:
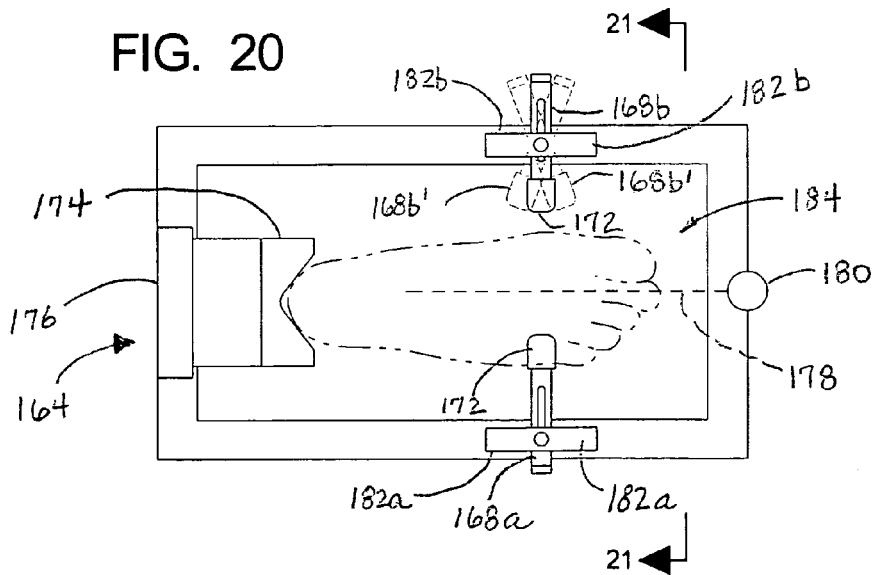
FIG. 20 is a plan view of the foot imaging apparatus of FIGS. 18-19, taken along line 20-20 in FIG. 18, showing the relationship of the foot to the alignment section and also to the aperture for the optical imaging section of the apparatus.
Figure 21:
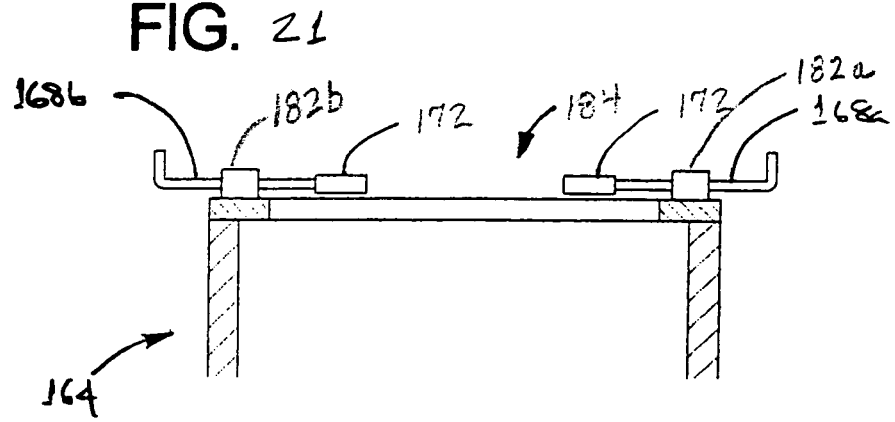
FIG. 21 is a cross-sectional view of the alignment section of the foot imaging apparatus of FIGS. 18-19, taken along line 21-21 in FIG. 20, showing the structure of the supports for reactively loading the fifth metatarsal head of the foot in greater detail.
Figure 22:
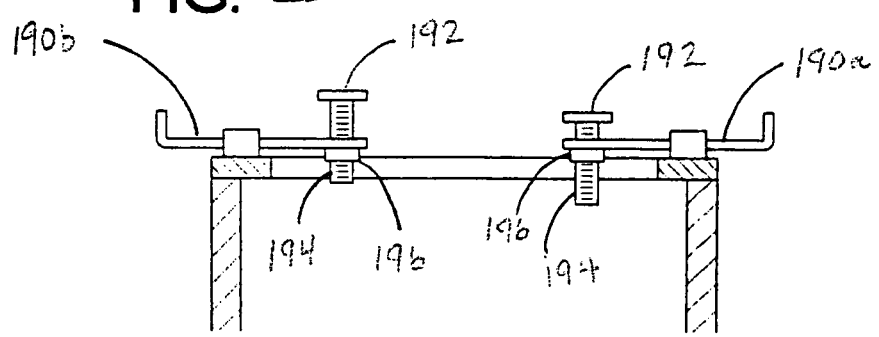
FIG. 22 is a cross-sectional view, similar to FIG. 21, of the alignment section of a foot imaging apparatus in accordance with another embodiment of the invention, in which the support members include adjustable height pads for engaging the fifth metatarsal head areas of the feet.

In the embodiment illustrated in FIGS. 18-21, the adjustable members are mounted for pivotable adjustment in brackets 182a, 182b at the sides of the aperture 184, as indicated by dotted line images 168a' and 168b' in FIG. 20 (see also FIG. 21). FIG. 22, in turn, shows an arrangement in which the alignment section includes adjustable supports 190a, 190b having head members 192 at their inboard ends that are vertically adjustable by means of shafts 194 that are in threaded engagement with cooperating nuts 196, to aid in adjusting the position of the plantar surface of the foot, and in particular with respect to the focal length of the camera of the imaging section. It will be understood that other forms of adjustable support members may occur to those skilled in the relevant art, and furthermore that although having the support members formed of a transparent material is preferable in terms of imaging accuracy, it is anticipated that in some instances opaque supports may be used instead and the obscured contours established by interpolation or other suitable means.

It is to be recognized that various alterations, modifications, and/or additions may be introduced into the constructions and arrangements of parts described above without departing from the spirit or ambit of the present invention as defined by the appended claims.

What is claimed is:

1. An apparatus for determining contours of a plantar surface of a patient's foot, said apparatus comprising:
    an imaging section for optically measuring contours of said plantar surface of said foot; and
    an alignment section for orientating said foot relative to said imaging section, said alignment section comprising:
        at least one support member for engaging said plantar surface of said foot substantially only beneath a lateral forefoot area of said foot, with said plantar surface of said foot directed towards said imaging section; and
        means for moving said foot relative to said at least one support member so that said lateral forefoot area of said foot is reactively loaded in a dorsal direction by said support member so as to lock a metatarsal joint of said foot.

2. The apparatus of claim 1, wherein said at least one support member comprises:
    at least one support member for engaging said plantar surface of said foot substantially only beneath a fifth metatarsal head area of said foot, so that said fifth metatarsal head area of said foot is reactively loaded in said dorsal direction by said support member.

3. The apparatus of claim 2, wherein said support member comprises:

a substantially transparent pad portion for engaging said plantar surface of said foot in said fifth metatarsal head area, so that said fifth metatarsal head area is exposed through said transparent pad to an optical sensor of said imaging section.

4. The apparatus of claim 3, wherein said at least one support member is positioned to support said foot in substantially centered alignment in an imaging area of said apparatus.

5. The apparatus of claim 4, wherein said at least one support member comprises:
a support member that is linearly adjustable to accommodate feet having different lengths.

6. The apparatus of claim 5, wherein said at least one support member comprises:
a support member that is laterally adjustable to accommodate feet having different widths.

7. The apparatus of claim 4, wherein said at least one support member comprises:
first and second adjustable support members mounted on right and left sides of said imaging area of said apparatus to support right and left feet in substantially centered alignment therein.

8. The apparatus of claim 7, wherein said imaging area comprises:
an imaging area that is located proximate a predetermined focal length of said imaging section, so that when a plantar surface of a foot is in engagement with one of said first and second support members said support member establishes a transverse plane of said foot at a location proximate said focal length of said imaging section.

9. The apparatus of claim 8, wherein said predetermined focal length is a predetermined focal length of a camera of said imaging section, said camera having a central plane that is substantially aligned with a centerline of said imaging area.

10. The apparatus of claim 9, wherein said alignment section further comprises:
a heel rest for centering a heel portion of said foot relative to said centerline of said imaging area.

11. The apparatus of claim 10, wherein said heel rest comprises:
a generally V-shaped heel stirrup substantially aligned with said centerline of said imaging area.

12. The apparatus of claim 11, wherein said heel stirrup is adjustably mounted so as to accommodate feet having different sizes.

13. The apparatus of claim 10, further comprising:
a laser pointer that generates a beam for alignment of said foot within said imaging area.

14. The apparatus of claim 13, wherein said beam that is generated by said laser pointer is aligned from said laser pointer to a center of said heel rest of said alignment section, so as to enable a subtalar joint of said foot to be placed in a neutral condition by bringing a second metatarsal head of said foot and a distal one-third of the lower leg into alignment with said beam.

15. The apparatus of claim 14, wherein said beam is aligned with said centerline of said imaging area.

16. The apparatus of claim 15, further comprising:
a wheeled carriage for rolling said apparatus away from said patient in response to distally-directed pressure exerted by said foot in said apparatus.

17. The apparatus of claim 16, wherein said wheeled carriage comprises:
means for allowing said carriage to be freely adjustable in a transverse plane of a floor so as to adjust alignment of said foot therein.

18. The apparatus of claim 17, wherein said means for allowing said carriage to be adjustable in said transverse plane of a floor comprises:
at least one pivotable caster mounted to said carriage.

19. The apparatus of claim 17, wherein said means for allowing said carriage to be adjustable in said transverse plane of a floor comprises:
at least one ball transfer unit mounted to said carriage.

20. A method for determining contours of a plantar surface of a patient's foot, said method comprising the steps of:
providing a support member proximate an imaging device for determining contours of said plantar surface of said foot;
moving said support member relative to said foot so as to apply a dorsally directed reactive force to substantially only a lateral forefoot area of said foot so as to lock a midtarsal joint of said foot; and
aligning said foot so that a subtalar joint of said foot is substantially in a neutral condition.

21. The method of claim 20, wherein the step of moving said support member relative to said foot so as to apply a dorsally-directed reactive force to substantially only a lateral forefoot area of said foot comprises:
moving said support member relative to said foot so as to apply a dorsally-directed reactive force to substantially only a fifth metatarsal head area of said foot.

22. The method of claim 21, wherein the step of moving said support member relative to said foot so as to apply a dorsally directed reactive force to said fifth metatarsal head area of said foot comprises the sequential steps of:
placing a rearfoot portion of said foot into engagement with said imaging device with said forefoot dorsiflexed and said heel extended forward; and
plantarflexing said foot so that said support member engages said fifth metatarsal head area to generate said dorsally-directed reactive force.

23. The method of claim 22, wherein the step of aligning said foot so that a subtalar joint of said foot is in a substantially neutral condition comprises:
aligning a second metatarsal head of said foot with a distal one-third of the lower leg so as to place said subtalar joint of said foot in said neutral condition.

24. The method of claim 23, wherein the step of aligning said second metatarsal head with said distal one-third of said lower leg comprises:
placing a rearfoot portion of said foot in engagement with said imaging device; and
adjusting a forefoot portion of said foot relative to said rearfoot portion so as to bring said second metatarsal head into alignment with said distal one-third of said lower leg.

25. The method of claim 24, wherein the step of adjusting said forefoot portion of said foot relative to said rearfoot portion so as to bring said second metatarsal head into alignment with said distal one-third of said lower leg comprises:
extending said patient's leg from a bent configuration in which a knee thereof is raised to a straightened configuration in which said knee is lowered, so as to move said imaging device distally and medially relative to said patient to a position in which said device is in coalignment with said second metatarsal head and said distal one-third of said lower leg.

* * * * *